United States Patent [19]
Selder et al.

[11] Patent Number: 5,682,892
[45] Date of Patent: Nov. 4, 1997

[54] JIG FOR POSITIONING AN INSTRUMENT TO BE INTRODUCED INTO AN OBJECT

[75] Inventors: Otto R. A. M. Selder; Aaldert J. Elevelt, both of Eindhoven, Netherlands

[73] Assignee: U.S. Philips Corporation, N.Y.

[21] Appl. No.: 639,861

[22] Filed: Apr. 26, 1996

[30] Foreign Application Priority Data

Apr. 26, 1995 [EP] European Pat. Off. ............ 95201076

[51] Int. Cl.$^6$ ...................................................... A61B 5/00
[52] U.S. Cl. ............................. 128/653.2; 128/653.1; 128/653.5; 128/662.05; 606/130; 324/318; 378/37
[58] Field of Search ...................... 128/653.1, 653.2, 128/653.5, 869, 749, 653, 662.05, 897; 324/318, 316; 606/130; 378/37

[56] References Cited

U.S. PATENT DOCUMENTS

| | | |
|---|---|---|
| 3,384,986 | 5/1968 | Rocha-Miranda et al. ............ 128/305 |
| 4,608,977 | 9/1986 | Brown ............................................ 128/303 |
| 5,056,523 | 10/1991 | Hotchkiss, Jr. et al. ................ 128/653 |
| 5,437,280 | 8/1995 | Hussman .................................. 128/653.2 |
| 5,534,778 | 7/1996 | Loos et al. ................................. 324/318 |

FOREIGN PATENT DOCUMENTS 0640842  3/1995  European Pat. Off. .

Primary Examiner—Marvin M. Lateef
Assistant Examiner—Eleni Mantis Mercader
Attorney, Agent, or Firm—Jack D. Slobod

[57] ABSTRACT

A jig for positioning an instrument, for example a biopsy needle, includes a stop (7) for defining the position of a free end (3) of the instrument in a first coordinate direction (Z) of a three-dimensional system of coordinates, and an adjusting mechanism (15, 17) for adjusting the position of the instrument in second (X) and third (Y) coordinate directions of the system of coordinates. The adjusting mechanism is accommodated in a housing (23) in which furthermore a phantom (5) is rigidly mounted. The adjusting mechanism includes a first and a second circular disc (15, 17), having a first and a second central axis (19, 21), respectively, each central axis extending perpendicularly to the plane of the relevant disc and through its center (16, 18). The first disc (15) is journalled in the housing (23) so as to be rotatable about the first central axis (19) and is provided with an eccentrically situated circular opening (27) whose diameter is substantially equal to the diameter of the second disc (17). The second disc (17) is journalled in said opening (27) so as to be rotatable about the second central axis (21). The first and second central axes (19, 21) extend parallel to the first coordinate direction (Z) and the first central axis intersects the plane of the second disc (17) at a distance (d) from the center (18) of the second disc which is smaller than the radius (r) of the second disc. At the same distance (d) from the center (18) a passage (29) is provided in the second disc (17), which passage is arranged to guide the instrument (1) in the first coordinate direction (Z).

8 Claims, 2 Drawing Sheets

JIG FOR POSITIONING AN INSTRUMENT TO BE INTRODUCED INTO AN OBJECT

BACKGROUND OF THE INVENTION

1. Field of the Invention

The invention relates to a jig for positioning an instrument to be introduced into an object to be examined, comprising a stop for defining the position of a free end of the instrument in a first coordinate direction of a three-dimensional system of coordinates, and adjusting means for adjusting the position of the instrument in second and third coordinate directions of the system of coordinates, said adjusting means being accommodated in a housing in which furthermore a phantom is rigidly mounted.

2. Description of the Related Art

A jig of this kind is known from EP-A-0 640 842. The jig is suitable for cooperation with an apparatus for forming images of internal parts of an object to be examined, for example a part of the body of a patient to be examined. To this end, first an image is formed in which the phantom is visible together with an object to be treated or examined, for example a tumor in the body. The position of the tumor in the system of coordinates can be determined from the relative positions of the phantom and the tumor in said image. The instrument is, for example a needle for performing a biopsy; on the basis of the data derived from the image, the instrument can be positioned so that its active part (the tip of the needle in the case of a biopsy needle) arrives exactly at the location of the tumor. The adjusting means of the known jig comprise a perforated plate in which the holes are arranged in a matrix extending according to the second and third coordinate directions. The instrument can be inserted into the holes either directly or by means of a holder. The distance between the holes determines the resolution with which the instrument can be positioned in the second and third coordinate directions. Because this resolution is insufficient in many cases, the plate is preferably mounted so as to be continuously adjustable in said coordinate directions. Therefore, for each of the second and third coordinate directions it is first necessary to select the hole situated nearest to the desired position, after which the plate must be displaced so that this hole is situated exactly in the desired position. This is a comparatively complex and time-consuming procedure which is also error prone.

SUMMARY OF THE INVENTION

It is an object of the invention to provide a jig of the kind set forth which enables fast and easy positioning of the instrument in the second and third coordinate directions also. To achieve this, the jig in accordance with the invention is characterized in that the adjusting means comprise a first and a second circular disc, having a first and a second central axis, respectively, each central axis extending perpendicularly to the plane of the respective disc and through its center, the first disc being journalled in the housing so as to be rotatable about the first central axis and being provided with an eccentrically situated circular opening whose diameter is substantially equal to the diameter of the second disc, the second disc being journalled in said opening so as to be rotatable about the second central axis, the arrangement being such that the first and second central axes extend parallel to the first coordinate direction and the first central axis intersects the plane of the second disc at a distance from the center of the second disc which is smaller than the radius of the second disc, a passage being provided in the second disc at the same distance from the center, said passage being arranged to guide the instrument in the first coordinate direction. As a result of these steps, the passage for guiding the instrument can be continuously displaced across a circular region whose center coincides with the center of the first disc and whose diameter amounts to twice the diameter of the second disc. To this end, the first and second discs are rotated, from a zero position, through angles which can be simply calculated from the coordinates of the object to be treated or examined which have been determined on the basis of the previously formed image.

The discs can be rotated, for example by means of a suitable drive; however, the simplest solution is to rotate the discs directly by hand. In order to facilitate correct adjustment of the discs, a preferred embodiment of the jig in accordance with the invention is characterized in that the housing and the first and second discs are provided with marks which are arranged to indicate the rotation of the first and the second disc about the first and the second central axis, respectively, with respect to a zero position.

For adjustment of the discs preferably first the first disc is rotated to the desired position, and subsequently the second disc. In order to prevent unintentional rotation of the first disc during rotation of the second disc, a further embodiment of the jig in accordance with the invention is characterized in that there is provided a locking device for locking the first disc with respect to the housing.

A further embodiment of the jig in accordance with the invention is characterized in that the phantom contains a material which has been chosen so as to enable imaging of the phantom by means of a magnetic resonance apparatus, and that the jig is rigidly connected to an RF coil for receiving RF signals emitted by the object to be examined. Because the jig is rigidly connected to the RF coil, a known magnetic resonance apparatus can form a precision image of the phantom together with the object to be treated.

These and other aspects of the invention will be apparent from and elucidated with reference to the embodiments described hereinafter.

DETAILED DESCRIPTION OF THE PREFERRED EMBODIMENTS

Figure 1:
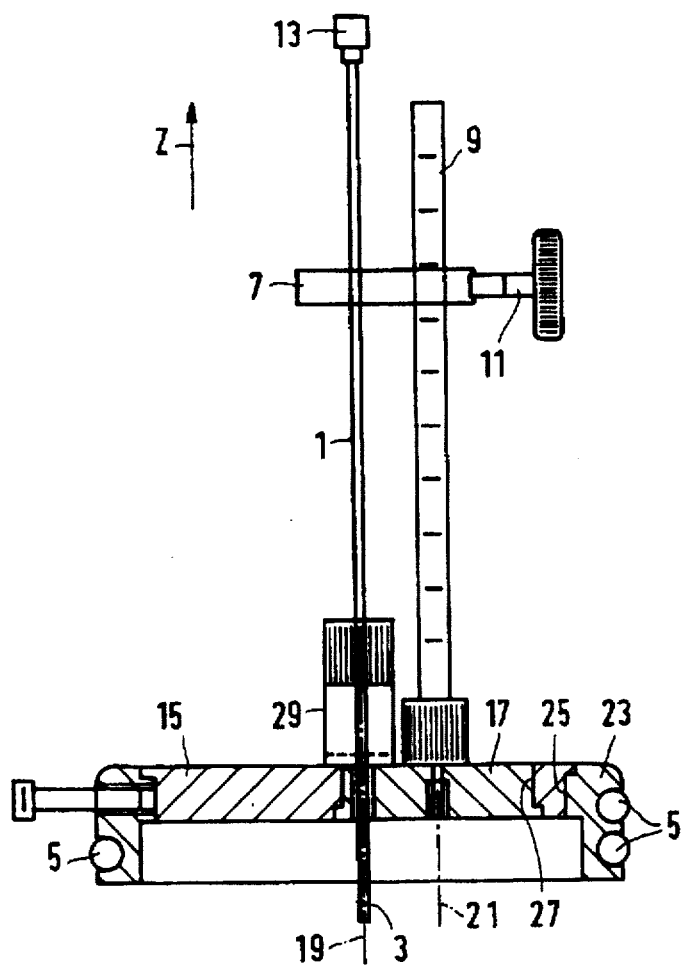
FIG. 1 is a cross-sectional view of an embodiment of a jig in accordance with the invention.
Figure 2:
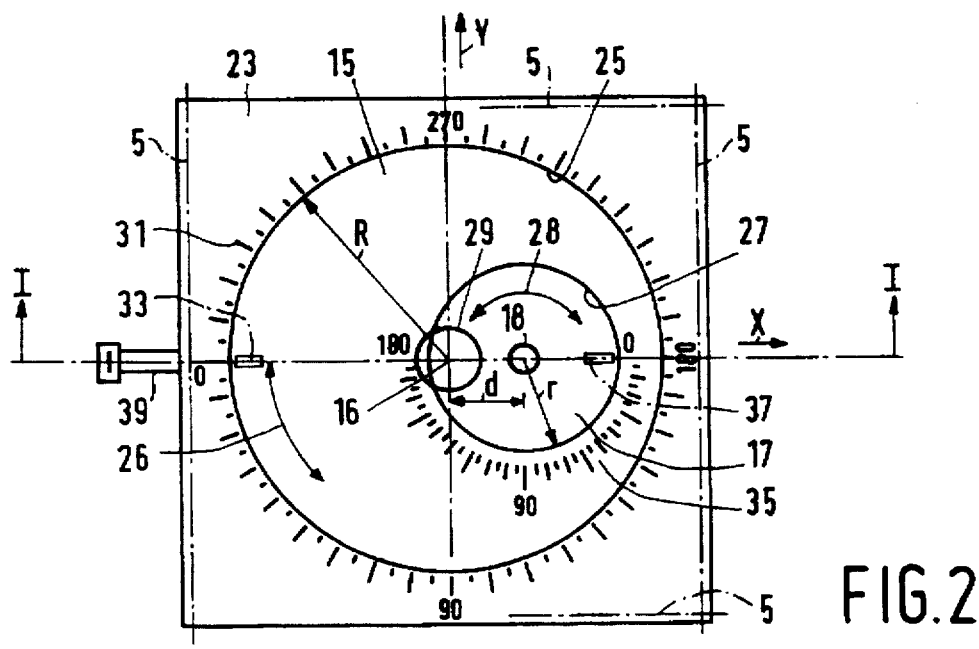
FIG. 2 is a plan view of the jig shown in FIG. 1.

The jig shown in the FIGS. 1 and 2 serves to position an instrument 1, for example a biopsy needle. The instrument 1 should be positioned so that the active part of the instrument, being the tip of the biopsy needle in the present example, reaches a predetermined location in an object to be examined (not shown). To this end, the jig comprises a phantom 5 which consists, for example of a number of rods of a material which is chosen so that it can be suitably imaged by means of an apparatus for forming medical images of the internal part of, for example a human or animal body. The location of the rods is denoted by dash-dot lines in FIG. 2. For example, if the jig is intended to cooperate with a magnetic resonance apparatus, a material having a high hydrogen content can be chosen for manufacturing the phantom 5. If the jig is intended to cooperate with an X-ray apparatus, for example a so-called CT scanner, a material exhibiting a suitable X-ray absorption will be chosen.

The jig furthermore comprises a stop 7 for defining the position of the free end 3 of the instrument 1 in a first coordinate direction of a three-dimensional system of coordinates, in this case being the Z direction of a cartesian system of coordinates. The stop 7 is displaceable along a rod 9 with a scale graduation and can be locked in a selected position by means of a locking device 11 which is known per se. The stop 7 cooperates with a thickened portion 13 at the end of the instrument 1 which is remote from the free end 3.

For adjustment of the position of the instrument 1 in the other coordinate directions (in this case the X and Y directions as indicated in FIG. 2), the jig also includes adjusting means which comprise a first circular disc 15 having a center 16 and a second circular disc 17 having a center 18. The radius of the first disc 15 is denoted by the letter R in FIG. 2 and the radius of the second disc 17 is denoted by the reference r. The first disc 15 has a central axis 19 which extends through its center 16 and the second disc 17 has a second central axis 21 which extends through its center 18. Each of the central axes extends perpendicularly to the plane of the relevant disc. The discs 15, 17 are oriented so that the first and second central axes 19, 21 extend parallel to the first coordinate direction, in this case being the Z direction. In the position of the adjusting means shown in FIG. 2, the first axis 19 coincides with the longitudinal axis of the instrument 1. The first disc 15 is journalled in a housing 23 so as to be rotatable about the first central axis 19, said housing being shaped as a substantially cubic block having a central opening 25 whose diameter is substantially equal to the diameter 2R of the first disc. The first disc 15 can rotate counterclock-wise and clock-wise as indicated by a double arrow 26. The phantom 5 is also accommodated in the housing 23. The first disc 15 comprises an eccentrically situated opening 27 whose diameter is substantially equal to the diameter 2r of the second disc 17 and in which the second disc is journalled so as to be rotatable about the second central axis 21. The second disc 17 can also rotate counterclock-wise as well as clock-wise as indicated by the double arrow 28. The first central axis 19 intersects the plane of the second disc 17 at a distance d from the center 18 of the second disc, which distance is smaller than the radius r of the second disc. At the same distance from the center 18 the second disc 17 is provided with a passage 29 which serves to guide the instrument 1 in the first coordinate direction. The passage 29 of the present embodiment is formed by a bush which is arranged on an opening in the second disc 17 and which comprises a central passage opening whose diameter is substantially equal to the outer diameter of the biopsy needle 1.

The upper surface of the housing 23 is provided with a first scale graduation 31 which cooperates with a first mark 33 on the upper surface of the first disc 15 so as to indicate the angular position of the first disc. The first scale graduation 31 is calibrated in degrees and the zero point is situated at the left in FIG. 2. When the first mark 33 is situated opposite the zero point of the first scale graduation 31, as shown in FIG. 2, the first disc 15 occupies a zero position. The center 18 of the second disc 17 is then situated on the X axis of the system of coordinates. On the upper surface of the first disc 15 there is provided a second scale graduation 35 which is situated around the opening 27 and cooperates with a second mark 37 on the upper surface of the second disc 17. The second scale graduation is also calibrated in degrees and its zero point is situated diametrically opposite the first mark 33. When the second mark 37 is situated opposite the zero point of the second scale graduation 35, the second disc 17 occupies a zero position. In FIG. 2 both discs 15, 17 are shown in the zero position. The passage 29 is then situated at the point (0,0) of the X-Y plane of the system of coordinates. The passage 29 can be moved to any point of the X-Y plane, within a circle having a radius 2d and the point (0,0) as its center, by successively rotating the first disc 15 and the second disc 17 through a predetermined angle. The relationship between the rotation of the two discs and the X and Y coordinates of the passage 29 will be described in detail hereinafter with reference to FIG. 3. In order to prevent displacement of the first disc 15 during rotation of the second disc 17, there is provided a locking device 39 for locking the first disc relative to the housing 23. The locking device 39 is formed, for example by a screw which can be screwed into the housing 23 from the side, thus clamping down the first disc 15.

Figure 3:
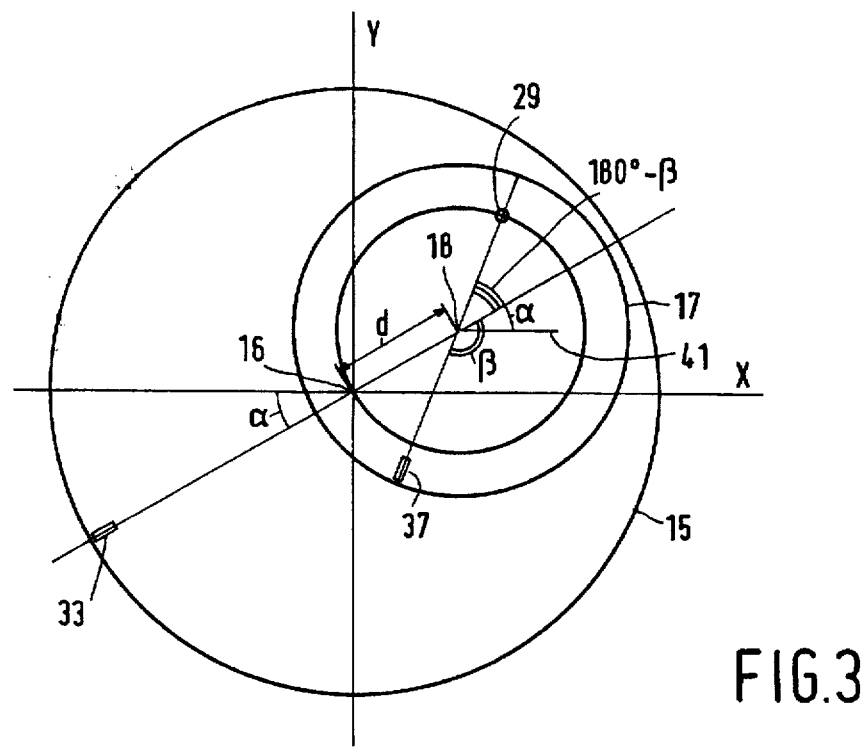
FIG. 3 shows a diagram illustrating the positioning of an instrument, using the jig shown in the FIGS. 1 and 2, according to coordinates in a rectangular system of coordinates.

FIG. 3 shows diagrammatically the X-Y plane of the system of coordinates, together with the first and second discs 15, 17. The figure also shows the positions of the first and second marks 33, 37 and of the passage 29. The first and second scale graduations 31, 35 have been omitted for the sake of clarity. The angular positions of the first and second discs 15, 17, which can be read by means of said scale graduations, however, are shown. The angular position of the first disc 15 is $\alpha$ and that of the second disc 17 is $\beta$. The coordinates of the passage 29 can be simply calculated from the values of $\alpha$ and $\beta$. It will be evident that the coordinates of the center 18 of the second disc 17 satisfy:

$$x_{18} = d.\cos\alpha \text{ and } y_{18} = d.\sin\alpha \qquad (1)$$

If a line 41 is drawn parallel to the X axis, starting from the center 18 of the second disc 17, the direction in which the passage 29 is situated encloses an angle of $180° - \beta + \alpha$ with respect to this line, viewed from the center 18. If the distances between the passage 29 and the center 18 of the second disc 17 in the X and the Y directions are denoted by the references $s_x$ and $s_y$, respectively, it holds that:

$$s_x = d.\cos(180° + \alpha - \beta) = -d.\cos(\alpha - \beta) \text{ and } s_y = d.\sin(180° + \alpha - \beta) = d.\sin(\beta - \alpha) \qquad (2)$$

The coordinates $x_{29}$ and $y_{29}$ of the passage 29 are:

$$x_{29} = x_{18} + s_x = d.\cos\alpha - d.\cos(\alpha - \beta) \text{ and}$$
$$y_{29} = y_{18} + s_y = d.\sin\alpha + d.\sin(\beta - \alpha) \qquad (3)$$

Thus, the coordinates of the passage 29 can be simply calculated from the angular rotation of the discs 15, 17. Conversely, the rotation necessary for the adjustment of given coordinates can also be simply calculated. Such a calculation can be carded out, for example on site by a calculator or the result can be laid down in advance in a table associated with the jig. The rotation of the discs 15, 17 can be performed simply by hand, but known drive mechanisms can also be built into the housing 23 for this purpose.

Figure 4:
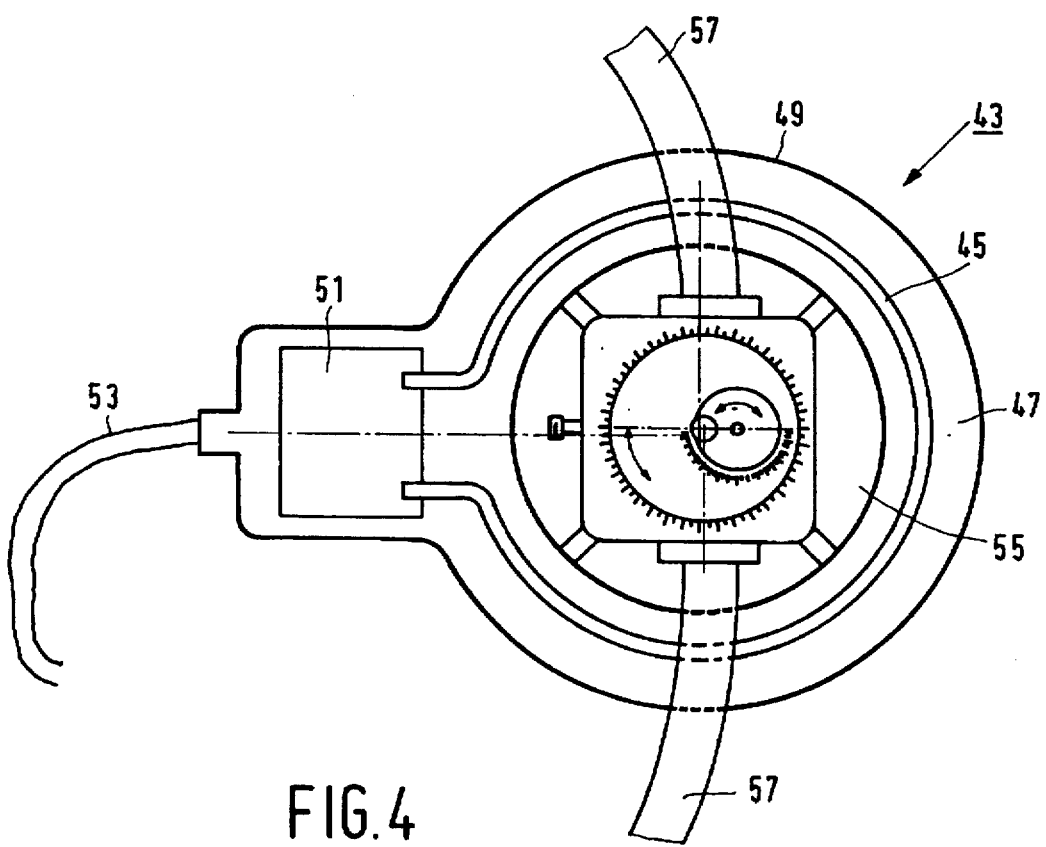
FIG. 4 is a plan view of an RF coil for a magnetic resonance apparatus and a jig connected to said RF coil.

FIG. 4 is a view of an RF coil 43 for receiving RF signals emitted, after their excitation, by nuclei in an object to be examined by means of a magnetic resonance apparatus. The RF coil 43 is a so-called surface coil which is formed, for example by at least one electric conductor 45 which is provided on an electrically insulating board 47 accommodated in a housing 49. The conductor 45 is connected, via a circuit 51, to a cable 53 which connects the RF coil 43 to the MR apparatus (not shown). Near the center of the board 47 a jig of the kind set forth is rigidly connected to the housing 49 and is enclosed by the conductors 45. It is alternatively possible to construct the jig and the RF coil 43 as separate components; the jig can then be positioned, for example freely in an opening 55 formed in the RF coil. It is important that at least the jig occupies a fixed position relative to an object to be examined, for example a patient. To this end, the jig is preferably provided with fixation straps 57 whereby it can be secured to a part of the body of the patient. When an image of an object to be examined is formed by means of such a construction, the phantom 5 is also imaged. Should, for example, a tumor be present in the body of the patient, the position of the tumor with respect to the phantom can be accurately determined in the image obtained. The coordinates of the tumor can thus be determined. Subsequently, the instrument 1 can be positioned so that its active part (for example, the tip 3 of the biopsy needle) can reach the location of the tumor. To this end, first the X and Y coordinates of the passage 29 are adjusted, as described with reference to FIG. 3, by rotation of the discs 15, 17, and subsequently the Z coordinate is adjusted by adjustment of the stop 7. If the instrument 1 is then introduced into the body of the patient as far as the stop 7, the tip 3 will exactly reach the tumor, so that a biopsy can be carded out.

The described jig can be built into, for example a supporting member for supporting of a part of a patient. The jig, or the surface coil provided with the jig as described with reference to FIG. 4, may constitute a separate accessory of a magnetic resonance apparatus. Corresponding considerations apply if the jig is arranged to cooperate with, for example an X-ray apparatus or an apparatus for forming images by means of ultrasound.

We claim:

1. A jig for positioning an instrument to be introduced into an object to be examined, comprising a stop for defining the position of a free end of the instrument in a first coordinate direction of a three-dimensional system of coordinates, and adjusting means for adjusting the position of the instrument in second and third coordinate directions of the system of coordinates, said adjusting means being accommodated in a housing in which furthermore a phantom is rigidly mounted, wherein the adjusting means comprise a first and a second circular disc having a first and a second central axis respectively, each central axis extending perpendicularly to the plane of the respective disc and through its center, the first disc being journalled in the housing so as to be rotatable about the first central axis and being provided with an eccentrically situated circular opening whose diameter is substantially equal to the diameter of the second disc, the second disc being journalled in said opening so as to be rotatable about the second central axis, the arrangement being such that the first and second central axes extend parallel to the first coordinate direction and the first central axis intersects the plane of the second disc at a distance from the center of the second disc which is smaller than the radius of the second disc, a passage being provided in the second disc at the same distance from the center, said passage being arranged to guide the instrument in the first coordinate direction.

2. A jig as claimed in claim 1, wherein the housing and the first and second discs are provided with marks which are arranged to indicate the rotation of the first and the second disc about the first and the second central axis respectively, with respect to a zero position.

3. A jig as claimed in claim 2, further comprising a locking device for locking the first disc with respect to the housing.

4. A jig as claimed in claim 3, wherein the phantom contains a material which has been chosen so as to enable imaging of the phantom by means of a magnetic resonance apparatus, and that the jig is rigidly connected to an RF coil for receiving RF signals emitted by the object to be examined.

5. A jig as claimed in claim 2, wherein the phantom contains a material which has been chosen so as to enable imaging of the phantom by means of a magnetic resonance apparatus, and that the jig is rigidly connected to an RF coil for receiving RF signals emitted by the object to be examined.

6. A jig as claimed in claim 1 further comprising a locking device for locking the first disc with respect to the housing.

7. A jig as claimed in claim 6, wherein the phantom contains a material which has been chosen so as to enable imaging of the phantom by means of a magnetic resonance apparatus, and that the jig is rigidly connected to an RF coil for receiving RF signals emitted by the object to be examined.

8. A jig as claimed in claim 1, wherein the phantom contains a material which has been chosen so as to enable imaging of the phantom by means of a magnetic resonance apparatus, and that the jig is rigidly connected to an RF coil for receiving RF signals emitted by the object to be examined.

* * * * *